(12) United States Patent
Reinhold et al.

(10) Patent No.: US 8,201,554 B2
(45) Date of Patent: Jun. 19, 2012

(54) INHALATION DEVICE HAVING AN OPTIMIZED AIR FLOW PATH

(75) Inventors: Olaf Reinhold, Gulfview Heights (AU); Jeffrey P. Taub, Escondido, CA (US); Robert P. Lackey, Carlsbad, CA (US); Stephen F. Goodall, Carindale Queensland (AU)

(73) Assignee: Injet Digital Aerosols Limited, New South Wales (AU)

( * ) Notice: Subject to any disclaimer, the term of this patent is extended or adjusted under 35 U.S.C. 154(b) by 0 days.

(21) Appl. No.: 12/404,110

(22) Filed: Mar. 13, 2009

(65) Prior Publication Data

US 2009/0173341 A1    Jul. 9, 2009

Related U.S. Application Data

(63) Continuation of application No. 10/080,504, filed on Feb. 22, 2002, now abandoned.

(60) Provisional application No. 60/271,193, filed on Feb. 23, 2001.

(51) Int. Cl.
*B05B 17/06* (2006.01)
*A61M 11/00* (2006.01)

(52) U.S. Cl. ............................... 128/200.16; 128/200.14

(58) Field of Classification Search ............. 128/200.14, 128/200.16, 202.21, 203.27, 203.12, 203.15, 128/204.11, 204.12, 204.13, 205.21
See application file for complete search history.

(56) References Cited

U.S. PATENT DOCUMENTS

| | | |
|---|---|---|
| 455,614 A | 7/1891 | Gonzalez |
| 1,105,934 A | 8/1914 | Stevens |
| 1,272,579 A | 7/1918 | Todd |
| 2,084,299 A | 6/1937 | Borden |
| 2,086,588 A | 7/1937 | Robin et al. |
| 2,449,853 A | 9/1948 | Karp |
| 3,812,854 A | 5/1974 | Michaels et al. |
| 3,820,540 A | 6/1974 | Hirtz et al. |
| 3,970,250 A | 7/1976 | Drews |
| 4,653,494 A | 3/1987 | Ruderian |
| 4,685,968 A | 8/1987 | Palmer |
| 4,694,302 A | 9/1987 | Hackleman et al. |
| 4,735,217 A | 4/1988 | Gerth et al. |
| 4,922,901 A | 5/1990 | Brooks et al. |
| 5,047,084 A | 9/1991 | Miller et al. |
| 5,060,671 A | 10/1991 | Counts et al. |
| 5,062,892 A | 11/1991 | Halko |
| 5,144,962 A | 9/1992 | Counts et al. |

(Continued)

FOREIGN PATENT DOCUMENTS

EP    0289336 A3    11/1988

(Continued)

OTHER PUBLICATIONS

Cromolyn Sodium, http://www-nmcp.med.navy.mil/das/Pharmacy/formulatory/CromolynSodium.htm, accessed on Mar. 29, 2001, 7 pages total.

(Continued)

*Primary Examiner* — Kristen Matter

(74) *Attorney, Agent, or Firm* — Honigman Miller Schwartz and Cohn LLP

(57) ABSTRACT

A device for the pulmonary delivery of a compound comprising a reservoir for storing a compound, a system for generating particles of a desired size, and a housing comprising an inlet and an outlet between which is formed a substantially unobstructed airflow path.

23 Claims, 2 Drawing Sheets

U.S. PATENT DOCUMENTS

| | | | |
|---|---|---|---|
| 5,170,782 | A | 12/1992 | Kocinski |
| 5,206,219 | A | 4/1993 | Desai |
| 5,261,601 | A | 11/1993 | Ross et al. |
| 5,354,934 | A | 10/1994 | Pitt et al. |
| 5,388,574 | A | 2/1995 | Ingebrethsen |
| 5,399,341 | A | 3/1995 | Huland et al. |
| 5,404,871 | A | 4/1995 | Goodman et al. |
| 5,413,732 | A | 5/1995 | Buhl et al. |
| 5,429,302 | A | 7/1995 | Abbott |
| 5,443,059 | A | 8/1995 | Koch et al. |
| 5,485,828 | A | 1/1996 | Hauser |
| 5,514,670 | A | 5/1996 | Friedman et al. |
| 5,551,416 | A | 9/1996 | Stimpson et al. |
| 5,605,674 | A | 2/1997 | Purewal et al. |
| 5,622,162 | A | 4/1997 | Johansson et al. |
| 5,666,977 | A | 9/1997 | Higgins et al. |
| 5,670,999 | A | 9/1997 | Takeuchi et al. |
| 5,694,920 | A | 12/1997 | Abrams et al. |
| 5,715,866 | A | 2/1998 | Granger |
| 5,724,957 | A | 3/1998 | Rubsamen et al. |
| 5,743,252 | A | 4/1998 | Rubsamen et al. |
| 5,744,124 | A | 4/1998 | Klokkers-Bethke et al. |
| 5,808,637 | A | 9/1998 | Wenzel et al. |
| 5,865,185 | A | 2/1999 | Collins et al. |
| 5,894,841 | A | 4/1999 | Voges |
| 5,934,289 | A | 8/1999 | Watkins et al. |
| 5,970,974 | A | 10/1999 | Van Der Linden et al. |
| 5,985,309 | A | 11/1999 | Edwards et al. |
| 6,026,809 | A | 2/2000 | Abrams et al. |
| 6,028,208 | A | 2/2000 | Gao et al. |
| 6,062,212 | A | 5/2000 | Davison et al. |
| 6,095,134 | A | 8/2000 | Sievers et al. |
| 6,143,329 | A | 11/2000 | Kim |
| RE37,053 | E | 2/2001 | Hanes et al. |
| 6,214,873 | B1 | 4/2001 | Adachi et al. |
| 6,228,383 | B1 | 5/2001 | Hansen et al. |
| 6,325,063 | B1 * | 12/2001 | Volgyesi ............ 128/204.13 |
| 6,435,175 | B1 | 8/2002 | Stenzler |
| 6,451,285 | B2 | 9/2002 | Blondino et al. |
| 6,571,793 | B1 | 6/2003 | Nilsson |
| 6,676,931 | B2 | 1/2004 | Dugger, III |
| 7,040,314 | B2 | 5/2006 | Nguyen et al. |
| 2003/0064052 | A1 | 4/2003 | Waters et al. |
| 2003/0072717 | A1 | 4/2003 | Reinhold et al. |
| 2009/0022669 | A1 | 1/2009 | Waters et al. |

FOREIGN PATENT DOCUMENTS

| | | |
|---|---|---|
| EP | 0499344 A2 | 8/1992 |
| EP | 0518608 A1 | 12/1992 |
| JP | 59053565 | 3/1984 |
| WO | 9210990 A1 | 7/1992 |
| WO | 9500128 A1 | 1/1995 |
| WO | 9503034 | 2/1995 |
| WO | 9916419 A1 | 4/1999 |
| WO | 0000181 A1 | 1/2000 |

OTHER PUBLICATIONS

Egger-Heigold, "The Effect of excipients on Pharmacokinetic Parameters of Parenteral Drugs", Inaugural dissertation, 2005, Basel.

Goodall et al., "Aerosolisation of Protein Drugs Using Thermal Inkjet Technology", Australia.

McKenzie, Guest Speaker, Australian and New Zealand Society of Respiratory Science Inc., 2001 Annual Scientific Meeting, Brisbane, Queensland, Mar. 16-19, 2001 Scientific Programme, 6 pages total.

"Erythropoetin Kit," http://www.idsltd.com/zipped/ibl/re56011.html, pages 1-8, accessed Mar. 29, 2001.

University of Iowa, "Follicle Stimulating Hormone (FSH)," Laboratory Services Handbook, http://www.medicin.uiowa.edu/Path Handbook/handbook/test828.html, (2000), 1 page total.

Sydpath, "Follicle Stimulating Hormone (FSH)," SydPath http://www.sydpath.stvincents.com.au/spec db/ SydPathTestDetails 1Page359.html, Accessed on Mar. 29, 2001, 1 page total.

Erasems.com, "Helping to Erase Multiple Sclerosis," Avonex, http://www.erasems.com/avonex.htm 1-2, Accessed on Mar. 29, 2001, 2 pages total.

Researchd.com, "Human Cytokine/Growth Factor/Chemokines Sample Spec Sheets," Human Cytokine Index, http://www.researchd.com/cytokines/rdl3023.htm 1-3 (2001), 3 pages total.

4adi.com, "Human Follicle Stimulating Hormone (FSH)," http://www.4adi.com/kits/hormones/0200FSH.html 1-2, Accessed on Mar. 29, 2001, total 2 pages total.

Metachem, "Human Granulocyte Macrophage Colony Stimulating Factor (GM-CSF)," Human GM-CSF Product Details, http://www.metachem.co.uk/humanGMCSF prod details.htm, Accessed on Mar. 29, 2001, 1 page total.

Andersen, "Final Report on the Safety Assessment of PEG-5, -10, -16, -25, -30 and -40 Soy Sterol", International Journal of Toxicology, 2000 vol. 19, No. Supplement 1, pp. 29-46, ISSN 1091-5818, 1 page total.

Kassem et al., "Influence of Some Humectants on the Physical Characteristics of Solidified Sodium Stearate-Based Sticks", International Journal of Cosmetic Science, (1984) vol. 6, No. 1, pp. 13-32, ISSN 0142-5463, 1 page total.

Parker, Susan H., et al., "Growth Hormone Treatment: What to Expect," HGF-Growth Hormone Treatment, http://www.medhelp.org/web/growth.htm, pp. 1-3, accessed on Mar. 29, 2001, 3 pages total.

Vogt, G., et al., "Protein Thermal Stability: Hydrogen Bonds or Internal Packing?" Fold Des, 2:S40-46 http://www.basf-lynx.basf-lynx.de/htm/abstract/97414924.htm (1997).

Houlihan, Michael E., "Smoking/Nicotine," Nicotine http://www.dal.ca/~houlihan/smoking.htm, pp. 1-2, accessed on Mar. 29, 2001, 2 pages total.

Shieh et al., "Technology of Electroplating Copper with Low-k Material a-C:F for 0.15-um Damascene Interconnection", Proceedings of SPIE-The International Society for Optical Engineering (2000), 4181 (Challenges in Process Integration and Device Technology), pp. 335-342, ISSN 0277-786X, 1 page total.

Wilkinson, Deborah Pursuing Portomes: Large-Scale Protein Profiling Studies Reveal the Molecular Bases of Cellular Processess and Disease States, The Scientist, 14(12):28 http://www.the-scientist.com/yr2000/iun/profile1000612.html.

Wikipedia, Isopropyl Alchohol, Defition, 4 pages total, Retrieved online on Jan. 10, 2008 from http://www.wikipedia.com.

Medline Plus, "Cromolyn (Nasal)", http://medlineplus.nim.nih.gov/medlineplus/druginfo/cromolynnasal202167, html1-5 (1999), total 5 pages.

* cited by examiner

INHALATION DEVICE HAVING AN OPTIMIZED AIR FLOW PATH

CROSS-REFERENCE TO RELATED APPLICATION

This application claims the benefit of U.S. Provisional Application No. 60/271,193 filed Feb. 23, 2001 and is a continuation of U.S. patent application Ser. No. 10/080,504 filed on Feb. 22, 2002, which is now abandoned.

FIELD OF THE INVENTION

The present invention generally relates to a device for the pulmonary delivery of an aerosolized compound. The device is particularly suitable for the pulmonary delivery of a pharmaceutical compound but may be used for other purposes.

BACKGROUND OF THE INVENTION

The following description of the background of the invention is provided to aid in understanding the invention, but is not admitted to be or to describe prior art to the invention.

Recently there has been interest in developing devices and methods to systemically deliver pharmaceutical compositions, particularly those comprising a protein or peptide as the prophylactic or therapeutic agent, via or through the lungs of the patient. There are currently three primary device types for the delivery of pharmaceuticals to the respiratory tract.

One such device type is the metered dose inhaler ("MDI"). MDIs use pressurized gas or propellant to deliver a burst of the compound or pharmaceutical into the patient's mouth during inhalation. A second type is the dry powder inhaler ("DPI"). DPIs use a burst of air to draw a dose of inactive powder into the bronchial tract. A third device type is a nebulizer. Nebulizers deliver the pharmaceutical through generating an aerosol by atomizing a liquid.

These conventional device types, however, are not desirable for delivery of certain pharmaceuticals, particularly those intended for systemic administration to the patient. There are many reasons why these conventional devices are not desirable. For example, the precision of dose control and delivery of conventional devices such as MDIs, DPIs, and nebulizers is less accurate for pulmonary delivery, which is of particular concern where specific dosages or dosing regimens are required. Another reason is that pharmaceutical compositions often become attached to or stuck on the side of the device during delivery, thus decreasing the dosage. These devices are also dependent on user technique, which makes dosages variable from person to person and dose to dose.

Thus there is a need to provide devices that are capable of efficient, effective, and consistent delivery of desired dosages of a systemic pharmaceutical to a patient via the pulmonary route.

SUMMARY OF THE INVENTION

An embodiment of this invention provides devices for delivery of an aerosolized compound, such as a pharmaceutical compound, to a patient via the pulmonary route, using an electronic ejection device. An embodiment of this invention comprises air paths specifically designed to minimize turbulence.

Advantageously, an embodiment of the present invention provides less deposition of aerosolized compound within the inhaler and a more effective transfer of the dispensed material into the inhaled air stream.

One embodiment of the present invention relates to a device that comprises a reservoir for storing a compounds wherein a reservoir is fluidly connected to a system for generating liquid particles of a desired size (or size range) containing a compound. This system comprises an entry port and an element to generate particles of the desired size for ejection from an ejection head of the element. At least the ejection head of the particle-generating element is disposed within a housing designed to generate a substantially unobstructed airflow path, substantially non-turbulent airflow, or substantially laminar airflow for delivery of the compound. The housing comprises an inlet and an outlet, and provides for substantially unobstructed airflow between the ejection head and the outlet when air traverses the airflow path from inlet to outlet. In one embodiment, the ejection head is disposed in the airflow path downstream of the inlet and upstream from the outlet.

Another embodiment of the invention relates to a method for delivering an aerosolized compound to a patient using a device according to the invention. Such a method comprises inhaling air through such a device while the particle-generating system of the device is actuated. Use of the term "while" encompasses during, immediately thereafter, immediately before, or any such moment that is temporally closely related.

Another embodiment of the invention relates to a method for generating an air stream containing a compound. This method comprises drawing air through a device of the invention from inlet to outlet while actuating the particle-generating system of the device.

Further features and advantages of the invention as well as the structure and operation of various embodiments of the invention are described in detail herein with reference to the accompanying drawings.

BRIEF DESCRIPTION OF THE DRAWINGS

The present invention will be described with particular embodiments thereof, and references will be made to the drawings in which.

Figure 1:
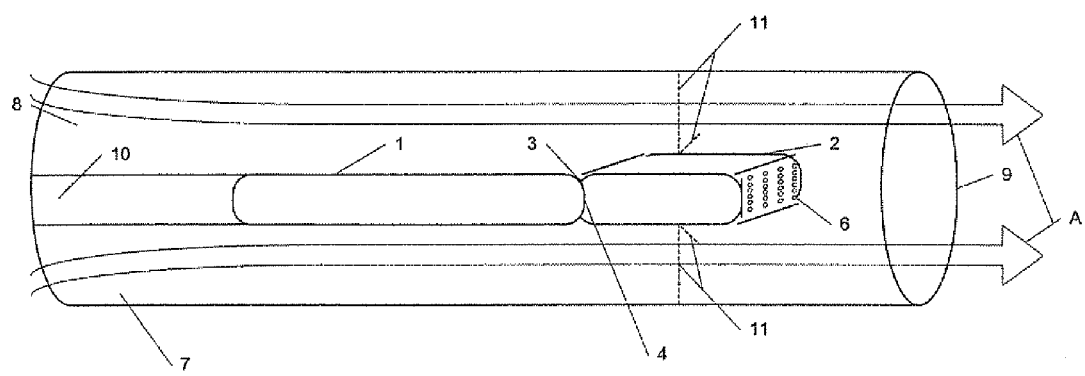
FIG. 1 illustrates one embodiment of the device according to the invention.

These drawings are included for illustrative purposes and are in no way intended to limit the scope of use or design of the invention.

DETAILED DESCRIPTION OF THE INVENTION

The reservoir and particle-generating system of a device according to the invention may be disposed within, partially within, or outside of the housing of the device. The reservoir, if included, within the housing, may be aerodynamically shaped. In another embodiment, the reservoir is detachable and/or replaceable. In another embodiment, the reservoir and particle-generating system are integrated into a single detachable and/or replaceable unit.

The system for generating particles can be any system that generates particles of the desired size or size range. In one embodiment, this system is a digitally controlled electronic droplet ejection device. Other embodiments of digitally controlled electronic droplet ejection devices useful in the practice of the invention include those that use heat or a piezoelectric component to generate particles that are ejected from the ejection head.

The size of the particles is a size that allows the particles to transit to and be deposited in the alveoli. This size may be where at least about 90% of the particles range in size from about 1 µm to about 5 µm such as where the particles have a mass median aerodynamic diameter of about 3 µm. For example, at least about 60% of the particles may have a mass median aerodynamic diameter of about 3 µm.

The housing may be of any size, shape and matter that allows for substantially unobstructed airflow. The airflow may be substantially laminar prior to exiting the housing outlet. The housing's inner surface proximal to the ejection head and extending to the outlet may be contoured to minimize turbulence. This substantially unobstructed airflow may comprise a substantially homogeneous mixture of the ejected compound and air in the airflow prior to exiting the housing outlet.

The term "reservoir" shall be interpreted to mean any container which is suitable to hold and store a compound. The reservoir may be of any shape, size, or material and may be aerodynamically designed so as to facilitate airflow and decrease obstructions in the airflow path. The relative size and optimal shape of the reservoir with respect to other components is variable. For example, altering the size and/or shape of the reservoir may have an impact on the aerodynamics of the system. The reservoir may have an outer layer of material which may be aerodynamically designed, and an inner collapsible bag which is suitable to hold and store a compound. The reservoir is filled with a compound to be administered and may be sealed or have a vent hole through the outer material to allow air displacement for the inner collapsible bag. The reservoir is fluidly connected to the system and may be either permanently connected or may be detachably connected so as to refill the reservoir with a compound.

The term "system" or "particle-generating system" shall be interpreted to mean any device that can act as an ejection means to eject particles into the airflow. By way of nonexclusive example, the system may compromise a piezoelectric device, such as the kinds (thermal and piezo) used in ink jet printing.

The term "particles" shall be interpreted to mean small droplets of the compound which are formed upon ejection from the ejection head of the element.

The term "desired size" shall be interpreted to mean a size which is sufficiently small such that when the particles are formed, they remain suspended in the air for a sufficient amount of time such that they may be inhaled and are sufficiently small such that the particles may be deposited in alveoli upon reaching the lungs. The particles may range in size from about 1 µm to about 5 µm in diameter, such as a mass median aerodynamic diameter of about 3 µm.

A compound stored in the reservoir of the system can be in any form, and is preferably a liquid formulation. The compound may be any pharmaceutical compound, for example, a protein, a small molecule, or a gene delivery vehicle. Preferred protein embodiments include EPO, G-CSF, GM-CSF, insulin, hGH, factor VIII, PSH, LH, VEGF, an interferon, an interleukin, an antibody or antibody fragment (alone or conjugated to another compound, for example, a cytotoxic agent). Small molecule embodiments include nicotine, methotrexate, albuterol, methadone, or cromylin. Still other embodiments of pharmaceutical compounds include a gene delivery vehicle such as a virus, a liposome, a nucleic acid, a nucleic acid complex, or suspensions thereof.

The term "compound" shall be interpreted to mean any fluid or liquid formulation such as any pharmaceutical compound.

The term "small molecule" shall be interpreted to mean any molecule having fewer than one hundred (100) non hydrogen atoms, and having a molecular weight of less than about 1 kDalton.

The term "fluidly connected" shall be interpreted to mean a connection whereby a fluid may be transferred from the reservoir to the system. This fluid connection may be accomplished in any known way. Non-exclusive examples of such a connection are gravity, a pump, a channel, or capillary feed.

The term "entry port" shall be interpreted to mean the area or point at which the compound enters the system.

The term "element to generate particles" shall be interpreted to mean any delivery engine which can generate particles of the desired size.

The term "ejection head" shall be interpreted to mean the area or point on the system where the particles of the compound are ejected into the air stream.

The term "housing" shall be interpreted to mean any casing or encased area in which air may flow.

The term "inlet" shall be interpreted to mean the area or point at which air enters the housing.

The term "outlet" shall be interpreted to mean the area or point at which air exits the housing.

The term "airflow path" shall be interpreted to mean the path that the air follows from the inlet to the outlet of the housing.

The term "disposed" shall be interpreted to mean that the ejection head is connected in any way to the housing such that the ejection head is downstream of the inlet and upstream of the outlet. This connection may be aerodynamically designed such as to decrease airflow obstructions and decrease turbulence in the airflow path.

The term "substantially unobstructed airflow" shall be interpreted to mean where the airflow path is substantially free of obstructions such as to decrease turbulence. By way of non-exclusive example, this may be accomplished by way of an aerodynamic airflow path.

The term "pharmaceutical compound" shall be interpreted to mean any molecule or combination of molecules which are capable of performing a pharmaceutical function, e.g., a drug or prodrug which is effective in helping to prevent or treat a disease or condition. "Effective in helping to prevent or treat a disease or condition" indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition. The term "pharmaceutical compound" includes but is not limited to any protein, small molecule or gene delivery system.

Prodrugs include chemical derivatives of a biologically-active parent compound which, upon administration, will eventually liberate the active parent compound in vivo. Use of prodrugs allows the artisan to modify the onset and/or duration of action in vivo. In addition, the use of prodrugs can modify the transportation into, the distribution or solubility of a drug in the body. Furthermore, prodrugs may reduce the toxicity and/or otherwise overcome difficulties encountered when administering a parent pharmaceutical compound.

Pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutically acceptable compositions for use in accordance with the present invention thus may be formulated in conventional ways using one or more physiologically acceptable carriers comprising excipients which facilitate processing of the active compounds into preparations which can be used pharmaceutically. Examples include but are not limited to surface tension-controlling agents, humectants, and viscosity-controlling agents; proper formulation may be dependent upon the specific pharmaceutical compound.

The term "gene delivery vehicle" shall be interpreted to mean any method of delivering an intact gene into an organism such as adenoviral particles or other viruses modified for gene delivery, naked DNA, degradable matrices, and/or such gene delivery systems as mentioned in Dan Luo and W. Mark Saltzman, Synthetic DNA Delivery Systems, Nature Biotechnology, January 2000, at 33-37, which is incorporated herein by reference in its entirety.

The term "electronic ejection device" shall be interpreted to mean any device which uses electronics to produce and eject particles of the desired size. The electronic ejection device includes, but is not limited to, a thermal device or a piezoelectric device such as those described in U.S. Pat. No. 5,894,841, which is incorporated herein by reference in its entirety.

The term "uses heat to generate particles" shall be interpreted to mean a thermal device which produces particles of the desired size using heat, such as described in U.S. Pat. No. 5,894,841. A typical thermal device comprises a liquid containing chamber provided with a configured array of nozzles and thin film resistors. A resistor is typically located directly behind each nozzle, for a given nozzle configuration. Each nozzle supplies a droplet or droplets (sometimes satellite droplets are created) of liquid from the chamber if and when a short electrical pulse energizes the corresponding resistor. The resistors thus function as an electronic ejection device. Within a few microseconds liquid in contact with the resistor is vaporized and forms a bubble. The vapor bubble grows rapidly and imparts momentum to liquid adjacent to a bubble. Some of this liquid is ejected as a droplet from an adjacent nozzle. The ejected volume of liquid is then automatically replaced in the chamber from the reservoir by a fluid connection.

The term "piezoelectric component" shall be interpreted to mean a device generating particles of the desired size by a pressure wave in the fluid produced by applying a voltage pulse to a piezoelectric ceramic which acts as an electronic ejection device. The fluid is ejected through a fine aperture. By way of non-exclusive example, a piezoelectric device is commonly used in inkjet printing.

The term "alveoli" shall be interpreted to mean components in the pulmonary region of the lung where gas exchange occurs between the air and the lungs and the circulatory system.

The term "substantially laminar" shall be interpreted to mean a substantially streamline steady flow at a substantially constant velocity. Air and entrained droplet flow is said to be laminar if the substance moves smoothly in layers, one layer (lamina) sliding relative to another. Viscosity and turbulence effects come into play if layers of the flowing substance change their shape as they move, as caused, for example, by airflow path surface irregularities, discontinuities, or the like.

The term "substantially homogeneous mixture" shall be interpreted to mean a mixture approaching uniform composition throughout.

The term "contoured to minimize turbulence" shall be interpreted to mean that the housing is designed such that turbulence is minimized and that airflow is approaching substantially constant or smooth laminar flow. By way of non-exclusive example, the inner walls of the housing may be sloped and/or smooth, or may be aerodynamically designed.

The term "aerosolized compound" shall be interpreted to mean a volume of air of which has suspended droplets comprising the compound within it. For example, the volume could be greater than 2 ml and less than 5 liters.

The term "substantially non-turbulent airflow" shall be interpreted to mean that the housing is designed so as to reduce and/or minimize turbulence.

Figure 2:
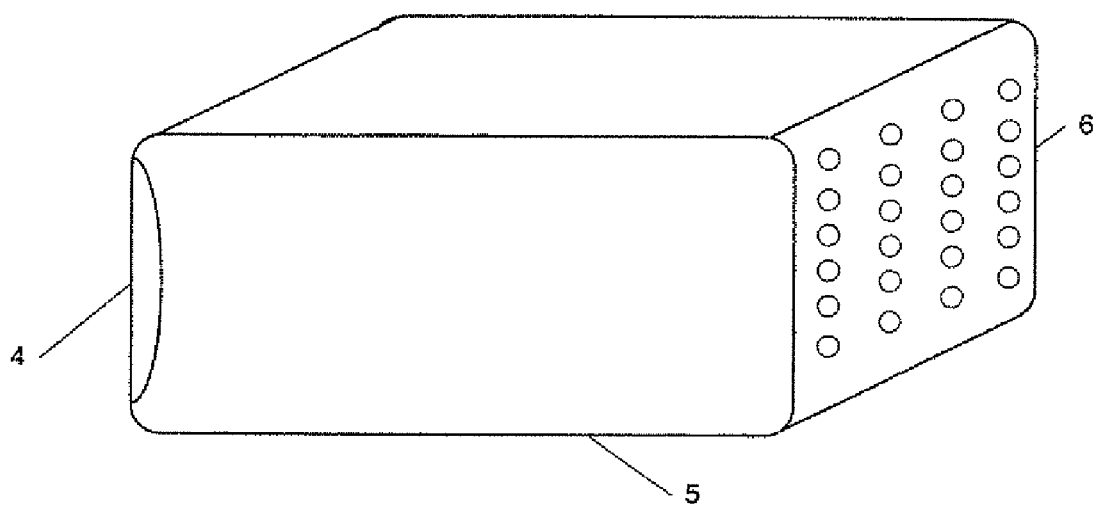
FIG. 2 illustrates a system to generate particles of the desired size according to an embodiment of the invention.

One embodiment of the device is presented in FIGS. 1-2. The device in FIG. 1 comprises a reservoir 1 for storing the compound to be delivered to the patient, a system 2 to generate particles of a desired size and a housing 7. The system FIG. 2 comprises an entry port 4 and an element 5 to general particles of the desired size for ejection from an ejection head 6 of the element. The housing comprises an inlet 8 and an outlet 9.

The reservoir 1 in this embodiment is disposed within and extends along the length of the housing 7 and is fluidly connected to the system 2 at the entry port 4 and is connected to the housing at the inlet 8 by connection to a power source 10 such as a battery. The reservoir 1 pictured is a collapsible bladder, however, other forms of a reservoir may be used. For example, the reservoir could be a cylinder fitted with a piston. The reservoir 1, in one embodiment, is sealed. The reservoir 1 may also be disposable and/or replaceable.

In one embodiment, system 2 is disposed entirely or partially within and extends along the length of the housing 7 and is disposed in the airflow path downstream of the inlet 8 and upstream from the outlet 9. The system 2 may also be connected to the housing by suspension-like attachments 11 so as to keep the airflow substantially unobstructed. The ejection head 6 of the system 2 is disposed in the airflow path upstream of the outlet so as to provide for a mixture area in which the compound, after ejection from the ejection head, mixes with the air flowing from the inlet 8 to the outlet 9 for delivery to the patient. In this embodiment, the element 5 to generate particles is of the kind used in a thermal ink jet printer. However, any device that will generate particles of the desired size may be used, such as those described in U.S. Pat. No. 5,894,841. The compound flows from the reservoir 1 into the element 5 through the entry port 4 and particles of the desired size are ejected from the ejection head 6 into the airflow path "A" which then delivers the compound to the patient. Moreover, element 5 may comprise a silicon wafer, and may be as thick or thin as needed.

For the pulmonary administration of pharmaceuticals, a small particle size is preferred. For example, particles ranging in size from about 1 μm to about 5 μm diameter are acceptable for the pulmonary delivery. Particles with a mass median aerodynamic diameter of about 3 μm are preferable. If necessary, the particle size can be reduced by an optional heating element which can be employed to vaporize the liquid. Particle size can further be reduced by directing the particles ejected from the ejection head 6 at each another or at a suitable target to further fragment the particles.

Housing 7 may provide for a substantially unobstructed airflow path so as to minimize turbulence so that the compound stored in the reservoir 1 may be efficiently delivered to the patient. Obstructions in the airflow path result in turbulence which results in some of the compound not reaching the patient. When there is turbulence, particles of the compound deposit on the side of the housing. Therefore, the physical shape and material of the components of the device may be altered so as to decrease turbulence. For example, the reservoir, system and housing may be aerodynamically designed.

The reservoir, system and housing may be constructed of materials that decrease turbulence. Suspension-like attachments 11 may be employed to secure the system to the housing to minimize obstructions and turbulence. Other forms of attachment may be used that minimize obstructions and turbulence.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application and all materials and information from any such articles, patents, patent applications, or other documents. The inventions illustratively described herein can suitably be practiced in the absence of any element or elements, limitation or limitations, not specifically disclosed herein. Thus, for example, the terms "comprising," "including", "containing", etc. shall be read expansively and without limitation. Additionally, the terms and expressions employed herein have been used as terms of description and not of limitation, and there is no intention in the use of such terms and expressions of excluding any equivalents of the future shown and described or portion thereof, but it is recognized that various modifications are possible within the scope of the invention claimed. Thus, it should be understood that although the present invention has been specifically disclosed by preferred embodiments and optional features, modification and variation of the inventions embodied therein herein disclosed can be resorted to by those skilled in the art, and that such modifications and variations are considered to be within the scope of the inventions disclosed herein. The inventions have been described broadly and generically herein. Each of the narrower species and subgeneric groupings falling within the generic disclosure also form part of these inventions. This includes the generic description of each invention with a proviso or negative limitation removing any subject matter from the genus, regardless of whether or not the excised materials specifically resided herein. Other embodiments are within the following claims. In addition, where features or aspects of an invention are described in terms of the Markush group, those schooled in the art will recognize that the invention is also thereby described in terms of any individual member or subgroup of members of the Markush group.

From the description of the invention herein, it is manifest that various equivalents can be used to implement the concepts of the present invention without departing from its scope. Moreover, while the invention has been described with specific reference to certain embodiments, a person of ordinary skills in the art would recognize that changes can be made in form and detail without departing from the spirit and the scope of the invention. The described embodiments are to be considered in all respects as illustrative and not restrictive. It should also be understood that the invention is not limited to the particular embodiments described herein, but is capable of many equivalents, rearrangements, modifications, and substitutions without departing from the scope of the invention.

What is claimed is:

1. A device for delivering an aerosolized compound, the device comprising:
    a housing comprising:
        an upstream end comprising an inlet;
        a downstream end positioned directly opposite and axially aligned with the upstream end and comprising an outlet, wherein the inlet and the outlet are axially aligned; and
        a body having an inner sidewall that extends from the upstream end to the downstream end, wherein the inner sidewall forms an axial bore having a substantially constant diameter, wherein the substantially constant diameter of the axial bore and the axially-aligned inlet and outlet results in a minimized turbulence and a steady, constant velocity airflow path extending through the axial bore from the inlet to the outlet;
    a reservoir that is configured to store the compound and disposed within the body between the upstream end and the downstream end such that the reservoir is in the airflow path downstream from the inlet and upstream from the outlet;
    a system disposed within the body between the upstream end and the downstream end such that the system is in the airflow path downstream of the inlet and upstream from the outlet, the system comprising;
        an entry port fluidly connected to the reservoir; and
        an element to generate particles of the compound of a desired size for physical ejection through one or more apertures from an ejection head of the element; and
    a suspension attachment extending between the inner sidewall of the body, in the airflow path downstream of the inlet and upstream from the outlet, connecting the system to the inner sidewall of the body such that the airflow is substantially unobstructed when between the system and the body.

2. A device according to claim 1 wherein the compound is stored in the reservoir in a liquid formulation.

3. A device according to claim 1 wherein the compound is a pharmaceutical compound.

4. A device according to claim 3 wherein the pharmaceutical compound is selected from the group consisting of a protein, a small molecule, and a gene delivery vehicle.

5. A device according to claim 3 wherein the pharmaceutical compound is a protein selected from the group consisting of a hormone, a receptor, an antibody, and an enzyme.

6. A device according to claim 3 wherein the pharmaceutical compound is a small molecule drug or prodrug.

7. A device according to claim 3 wherein the pharmaceutical compound is a gene delivery vehicle.

8. A device according to claim 1 wherein the reservoir is aerodynamically shaped.

9. A device according to claim 1 wherein the reservoir is detachable.

10. A device according to claim 1 wherein the reservoir and particle-generating system are integrated into a single detachable unit.

11. A device according to claim 1 wherein the particle-generating system is an electronic ejection device.

12. A device according to claim 11 wherein the electronic ejection device uses heat to generate particles ejected from the ejection head.

13. A device according to claim 11 wherein the electronic ejection device uses a piezoelectric component to generate particles ejected from the ejection head.

14. A device according to claim 1 wherein the desired size of the particles is a size that allows the particles to transit to and be deposited in alveoli.

15. A device according to claim 14 wherein at least about 90% of the particles range in size from about 1 p.m. to about 5 p.m.

16. A device according to claim 15 wherein at least about 60% of the particles have a mass median aerodynamic diameter of about 3 p.m.

17. A device according to claim 1 wherein the substantially unobstructed airflow is substantially laminar prior to exiting the housing outlet.

18. A device according to claim 1 wherein the substantially unobstructed airflow comprises a substantially homogeneous mixture of the ejected compound and air in the airflow prior to exiting the housing outlet.

19. A device according to claim 1 wherein an inner surface of the housing, proximal to the ejection head and extending to the outlet, is contoured to minimize turbulence.

20. A method of delivering an aerosolized compound to a patient, the method comprising inhaling air which contains a compound through a device while the particle-generating system of the device is actuated, wherein said device comprises:
   a housing comprising
      an upstream end comprising an inlet;
      a downstream end positioned directly opposite and axially aligned with the upstream end and comprising an outlet, wherein the inlet and the outlet are axially aligned; and
      a body extending from the upstream end to the downstream end, wherein an airflow path is formed through the body from the inlet to the outlet, and wherein the airflow path is circumscribed by an inner sidewall of the housing that extends between the upstream end and the downstream end, wherein the inner sidewall forms an axial bore having a substantially constant diameter, wherein the substantially constant diameter of the axial bore and the axially-aligned inlet and outlet results in airflow path extending through the axial bore such that the airflow path has a minimized turbulence and a steady, constant velocity;
   a reservoir configured to store the compound and disposed within the body between the upstream end and the downstream end such that the reservoir is in the airflow path downstream from the inlet and upstream from the outlet;
   a system disposed within the body between the upstream end and the downstream end such that the system is in the airflow path downstream of the inlet and upstream from the outlet, the system comprising;
      an entry port fluidly connected to the reservoir; and
      an ejection device to generate particles of the compound of a desired size for physical ejection through one or more apertures from an ejection head of the device; and
   a suspension attachment extending between the inner sidewall of the body, in the airflow path downstream of the inlet and upstream from the outlet, connecting the system to the inner sidewall of the body such that the airflow is substantially unobstructed when between the system and the body.

21. A method for generating an air stream comprising a compound according to claim 20, wherein the air is drawn from inlet to outlet.

22. A device for delivering an aerosolized compound, the device comprising:
   a system that generates particles of a desired size that comprise a compound, wherein the system is fluidly connected to a reservoir, wherein the system comprises an entry port and an element to generate particles of the desired size for physical ejection through one or more apertures from an ejection head of the element; and
   a housing having an upstream end, a downstream end directly opposite and axially-aligned with the upstream end, and a body connected to the upstream end and the downstream end, the body having an inner sidewall forming an axial bore substantially laterally extending from the downstream end to the upstream end, wherein a minimized turbulence, constant velocity airflow path extends through the axial bore, wherein the inlet is located at said upstream end of said housing and facing directly opposite to and axially-aligned with said outlet and in which at least the ejection head is disposed in the minimized turbulence, constant velocity air flow path downstream of the inlet and upstream from the outlet; and
   a suspension attachment extending between the inner sidewall of the body, in the airflow path downstream of the inlet and upstream from the outlet, connecting the system to the inner sidewall of the body such that the airflow is substantially unobstructed when between the system and the body.

23. A device for delivering an aerosolized compound, according to claim 22, wherein the housing provides for substantially laminar airflow between the ejection head and outlet when air traverses the airflow path from inlet to outlet.

* * * * *